Figure 1:
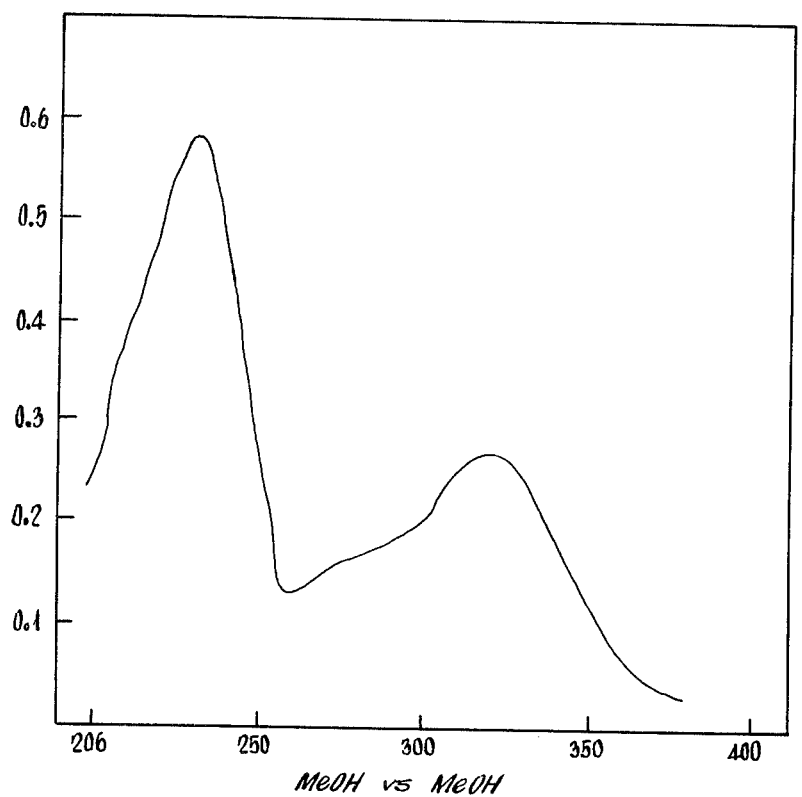

United States Patent [19]

Zimmerman et al.

[11] 4,175,007

[45] Nov. 20, 1979

[54] PROCESS FOR PRODUCING ANTIBIOTIC A21A

[75] Inventors: Sheldon B. Zimmerman, Springfield, N.J.; John H. Chalmers, Jr., Houston, Tex.

[73] Assignee: Merck & Co., Inc., Rahway, N.J.

[21] Appl. No.: 853,078

[22] Filed: Nov. 21, 1977

Related U.S. Application Data

[62] Division of Ser. No. 736,794, Oct. 29, 1976, Pat. No. 4,071,631.

[51] Int. Cl.² .............................................. C12D 9/14

[52] U.S. Cl. .................................. 435/105; 435/895; 435/118

[58] Field of Search ...................................... 195/80 R

[56] References Cited

U.S. PATENT DOCUMENTS

| 4,062,948 | 12/1977 | Vos et al. | 195/80 R |
| 4,065,356 | 12/1977 | Maiese et al. | 195/80 R |

*Primary Examiner*—Alvin E. Tanenholtz
*Attorney, Agent, or Firm*—Hesna J. Pfeiffer; Julian S. Levitt; Richard A. Thompson

[57] ABSTRACT

Antibiotic A21A is produced by cultivating *Stneptomyces filipinesis* under aerobic conditions.

6 Claims, 3 Drawing Figures

MeOH vs MeOH

WAVELENGTH (MICRONS)

PROCESS FOR PRODUCING ANTIBIOTIC A21A

This is a division of application Ser. No. 736,794 filed Oct. 29, 1976 now U.S. Pat. No. 4,071,631.

SUMMARY OF THE INVENTION

This invention relates to a new antibiotic agent A21A with antibacterial activity, growth-improving activity and to a method for its production. The antibiotic is obtained by cultivating *Streptomyces filipinensis*, MA-4581, in an aqueous nutrient medium comprising assimilable carbonhydrates and assimilable nitrogen sources under submerged aerobic conditions until substantial antibiotic is imparted to the medium.

The antibiotic is recovered by extracting the fermentation broth with a water immiscible polar or hydroxylic solvent. The solvent-extracted antibiotic is further purified by evaporation, precipitation and chromatography to yield substantially pure A21A.

DESCRIPTION OF THE INVENTION

This invention relates to a new antibiotic agent. More particularly, it is concerned with a new antibiotic substance herein called A21A. The invention encompasses the antibiotic in dilute forms, as crude concentrates and in pure forms.

It is an object of the present invention to provide a new and useful antibiotic which is highly effective in inhibiting the growth of various gram-negative and gram-positive microorganisms. Another object is to provide a process for the preparation of this novel antibiotic substance by the fermentation of nutrient media with a heretofore undescribed strain of the known microorganism, *Streptomyces filipinensis*. Other objects will be apparent from the detailed description of this invention hereinafter provided.

The novel antibiotic substance of the present invention is produced by growing under controlled conditions the microorganism *Streptomyces filipinensis*.

Based upon extensive taxonomic studies, *Streptomyces filipinensis*, isolated from a soil sample, was identified as an actinomycete and has been designated MA-4581 in the culture collection of MERCK & CO., Inc., Rahway, N.J. A culture thereof has been placed on permanent deposit with the culture collection of the Northern Regional Research Laboratories, Northern Utilization Research and Development Division, Agricultural Research Service, U.S. Department of Agriculture, Peoria, Ill., and has been assigned accession No. NRRL 11,044.

The classification keys for the genus *Streptomyces* and the culture descriptions of *Streptomyces* species found in Bergey's *Manual of Determinative Bacteriology* (7th Edition, 1957) and in *The Actinomycetes, Vol. II* (1961) by S. A. Waksman and in "Cooperative Descriptions of Type Cultures of *Streptomyces*" by E. B. Shirling and D. Gottlieb, *International Journal of Systematic Bacteriology*, 18, 69–189 (1968), 18, 279–392 (1968), 19, 391–512 (1969) and 22, 265–394 (1972) were searched for a *Streptomyces* species having morphological and cultural characteristics similar to those of MA-4581. In these aforementioned classical references, the *Streptomyces filipinensis* shows a close correlation with the A21A-producing culture MA-4581. Therefore, MA-4581 is designated *Streptomyces filipinensis*.

The morphological and cultural characteristics of *Streptomyces filipinensis* MA-4581 are set forth in the following table.

Morphology: Sporophores form branched spirals, both compact and open. Spores are in chains of more than 15 spores and are spherical to oval. Sporulation observed on oatmeal agar, egg albumin agar and inorganic saltsstarch agar.

(V=vegetative growth; A=aerial mycelium; SP=soluble pigment)

Oatmeal agar (ISP Medium 3)
V: Reverse—dark brown
A: Brownish—gray (4li) edged with non-sporulating white
SP: Light brown
Czapek Dox agar (sucrose nitrate agar)
V: Reverse—light brown
A: Moderate, sand—colored (3cb)
SP: Light reddish—brown
Egg albumin agar
V: Reverse—brown
A: Powdery, light brownish gray (4ig)
SP: Light brown
Clycerol asparagine agar (ISP Medium 5)
V: Tan
A: Sparse, brownish—white
SP: Light reddish—brown
Inorganic salts-starch agar (ISP Medium 4)
V: Reverse—brown edged with dark brown
A: Light brownish gray (4ig) edged with brownish-gray (4li)
SP: Light brown
Yeast extract-dextrose +salts agar
V: Reverse—dark brown
A: Brownish—white
SP: Brown
Yeast extract-malt extract agar (ISP Medium 2)
V: Reverse—dark brown
A: Brownish gray (4li) edged with non-sporulating white
SP: Dark brown
Peptone-iron-yeast extract agar
V: Dark brown
A: None
SP: Very dark brown
Melanin: Positive
$H_2S$ production: Positive
Nutrient agar
V: Tan
A: Sparse, grayish—white
SP: Light brown
Nutrient starch agar
V: Tan
A: Scant, whitish
SP: None
Hydrolysis of starch: Good
Nutrient gelatin agar
V: Tan
A: Scant, grayish
SP: Light brown
Liquefaction of gelatin: Good
Gelatin stabs
V: Tan
A: None
SP: Brown
Liquefaction of gelatin: Good
Skim milk agar
V: Dark brown A: None
SP: Dark brown
Hudrolysis of casein: Good
Litmus milk
V: Dark brown growth ring
A: None
Color: Dark purplish—brown
Coagulation and/or peptonization: Peptonization
Skim milk
V: Dark brown growth ring
A: None
SP: Dark brown
Coagulation and/or peptonization: Peptonization
Potato plug
V: Dark brown
A: Grayish, sparse
SP: Dark brown
Loeffler's Blood serum
V: Tan
A: None
SP: Brownish
Liquefaction: Moderate
Nutrient tyrosine agar
V: Dark brown
A: Sparse, grayish
SP: Dark brown
Decomposition of tyrosine: Positive All of the readings reported above were taken after three weeks incubation at 28° C. unless noted otherwise. The pH of the media used in these studies was approximately neutral, namely, pH 6.8–7.2. The color designations used in the description are in accordance with the definitions of the *Color Harmony Manual*, 4th Edition (1958), Container Corporation of America, Chicago, Illinois.

*Streptomyces filipinensis* MA-4581 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2). Table I shows the utilization of these carbohydrate sources by *Streptomyces filipinensis:* + *indicating good growth,* ± *indicating poor growth, and* − *indicating no growth on the particular carbohydrate.*

TABLE I

| Glucose | + | Maltose | + |
|---|---|---|---|
| Arabinose | + | Mannitol | + |
| Cellulose | − | Mannose | + |
| Fructose | + | Raffinose | + |
| Inositol | + | Rhamnose | + |
| Lactose | + | Sucrose | + |
| Xylose | + | | |

The amount of growth with change in temperature and the oxygen requirement of the microorganism is as follows:

Temperature range (Yeast extract-glucose + salts agar);
28° C.—good growth
37° C.—good growth
50° C.—no growth Oxygen requirement (Stab culture in yeast extract-glucose + salts agar);
Aerobic Antibiotic A21A is produced by cultivating *Streptomyces filipinensis* MA-4581 under submerged aerobic conditions in aqueous medium containing assimilable carbohydrates and nitrogen sources. The incubation temperature may range between 20° C. and 37° C. and the initial pH of the medium may be adjusted to between pH 5.0–8.0. The fermentation is carried out for approximately 72 to 144 hours, preferably for approximately 120 hours at which time the antibiotic has formed.

At the conclusion of the fermentation, the fermentation broth is brought to pH 5.0–5.3 with an acid such as hydrochloric acid. Between one-half and two volumes of a water immiscible polar or hydroxylic solvent is used to extract the fermentation broth to obtain the antibiotic A21A. Representative of such solvents are lower alkyl esters of lower alkanoic acids such as methyl formate, ethyl formate, methyl acetate, ethyl acetate, n-butyl acetate, isobutyl acetate, ethyl propionate; a ketone such as methyl ethyl ketone, or cyclohexanone, or a halogenated lower hydrocarbon such as chloroform, methylene chloride, carbon tetrachloride, ethylene dichloride, 1-chloro-2,2-dimethylpropane, tetrachloroethylene, bromoform; or a hydroxylic solvent such as n-butyl alcohol or isoamylalcohol.

More particularly said solvents are chloroform, n-butyl alcohol, methyl ethyl ketone or ethyl acetate. The solvent is separated from the aqueous phase and concentrated by evaporation in vacuo to a dark oil. This fraction is defatted with hexane which also precipitates the A21A.

The precipitate could be further purified by chromatography on silica gel using a chloroform:methanol:aqueous ammonia solvent (80:20:1).

Antibiotic A21A is an amorphous yellow powder soluble in polar and hydroxylic solvents such as chloroform, acetone, and the lower alcohols. It has prominent characteristic absorption peaks at approximately $\lambda=231$ nm, and $\lambda=322$ nm in the U.V. and contains no carbohydrate by the anthrone test.

The physical properties of A21A are: $\lambda(0.01 N HCl$ in methanol$)=322$ nm E%=328. 231 nm E%=722.

Analysis: C 65.23% H 7.78%; N 3.47%

Figure 2:
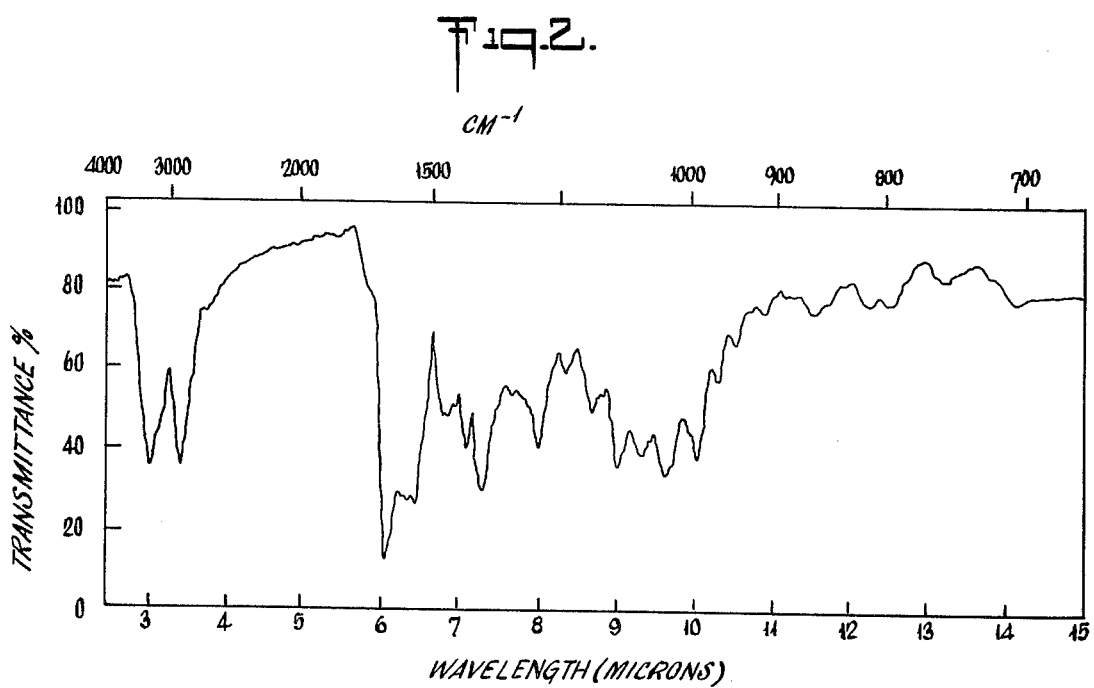
Figure 2:
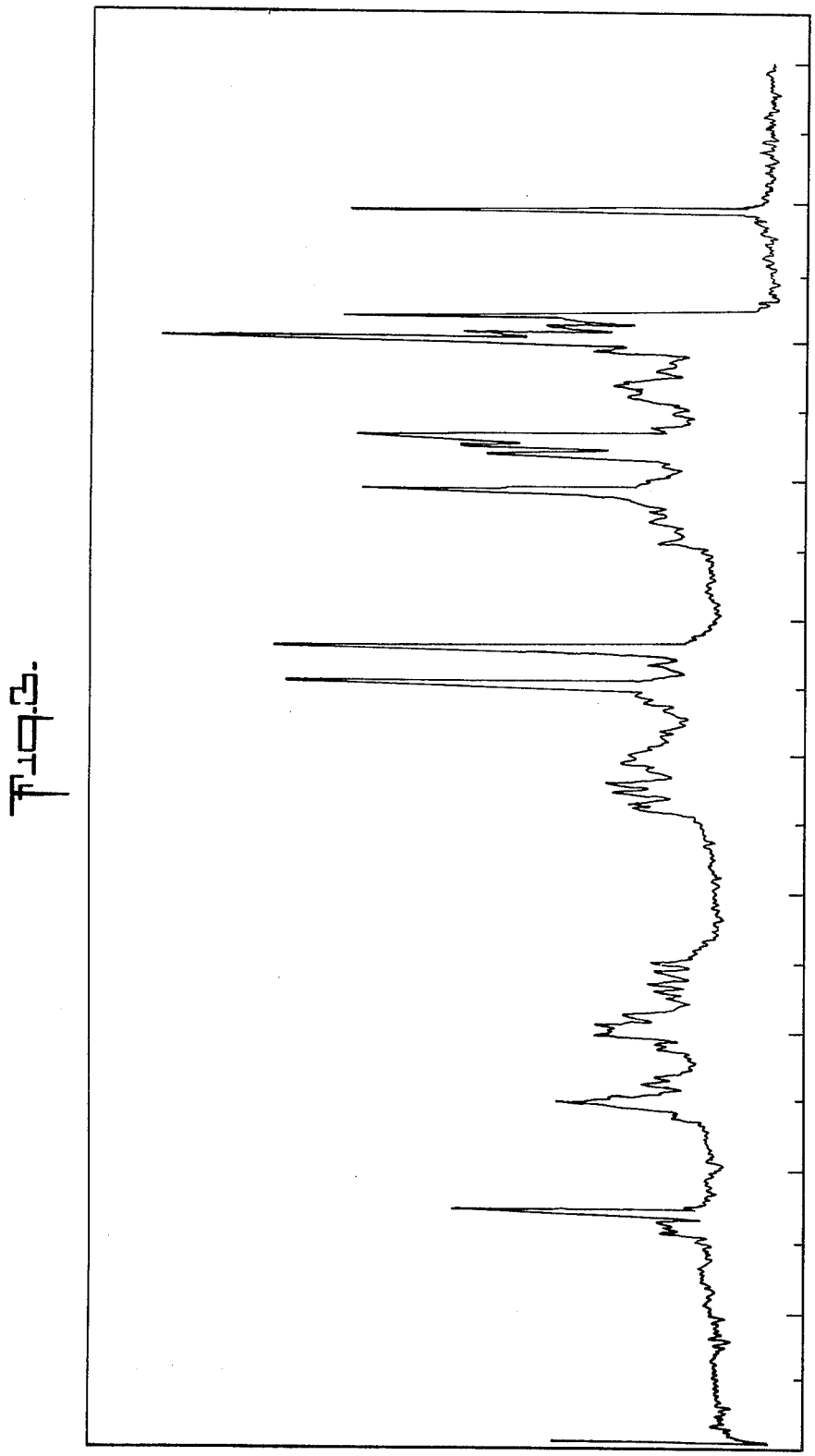

The U.V., I.R. and NMR spectra are shown in FIGS. 1, 2 and 3. The NMR spectra is taken in deuterated $CHCl_3$ with tetramethylsilane as internal reference.

A21A has the molecular structure as follows:

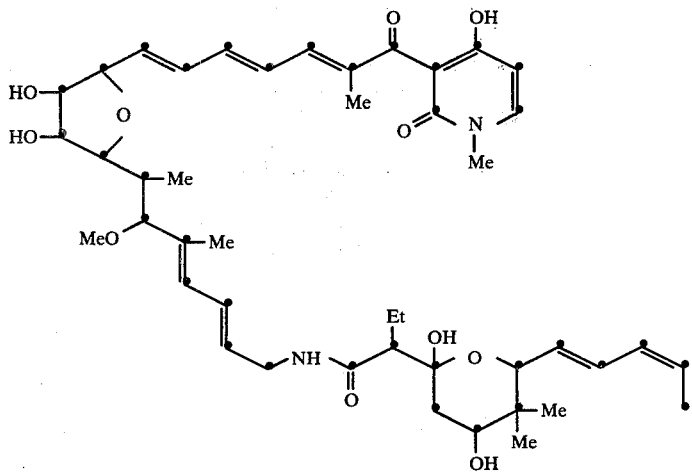

It is to be understood that for the production of the new antibiotic of this invention, the present invention is not limited to the organism Streptomyces filipinensis, MA-4581, or to organisms fully answering the above growth and microscopic characteristics which are given for illustrative purposes. In fact, it is desired and intended to include the use of mutants produced from the described organism by various means, such as X-radiation, ultraviolet radiation, nitrogen mustard, phage exposure and the like.

The novel antibiotic of the invention, A21A, is produced during the aerobic fermentation of suitable aqueous nutrient media under controlled conditions via the inoculation with the organism, Streptomyces filipinensis, MA-4581. Aqueous media, such as those employed for the production of other antibiotics are suitable for producing A21A. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, rye, cornstarch, corn meal and the like can be used either alone or in combination as sources of assimilable carbon in the nutrent medium. The exact quantity of the carbohydrate source or sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the examples are merely illustrative of the wide variety of media which may be employed, and are not intended to be limitative.

The fermentation is carried out at temperatures ranging from about 2° C. to 37° C.; however, for optimum results it is preferable to conduct the fermentation at temperatures of from about 22° C. to 30° C. The pH of the nutrient media suitable for growing the Streptomyces filipinensis MA-4581 culture and producing A21A can vary from about 5.0 to 8.0.

Although the novel antibiotic A21A is produced by both surface and submerged cultures, it is preferred to carry out the fermentation in the submerged state.

A small scale fermentation of the antibiotic is conveniently carried out by inoculating a suitable nutrient medium with the antibiotic-producing culture and, after transfer to a production medium, permitting the fermentation to proceed at a constant temperature of about 28° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for two days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from three to five days while agitating and/or aerating the nutrient medium and maintaining the temperature at about 24° C. This method of producing A21A is particularly suited for the preparation of large quantities of the antibiotic.

A21A is further characterized by the following antibiotic spectrum profile. A droplet of 0.015 ml. of purified chemical A21A is dissolved in 40% acetone water then placed on the surface of seeded agar plates. The results, expressed in terms of the diameter in millimeters of the zone of inhibition are as set forth in Table 1.

Table I

| Organism MB No. (ATCC) | Inhib. Zone Diam., mm. Chem. Prep. |
|---|---|
| Bacillus sp. 633 | 16 |
| Staphylococcus aureus 108 (6538P) | 11 |
| Bacillus subtilis 964 (6633) | 12 |
| Sarcina lutea 1101 (9341) | 30 |
| Staphylococcus aureus 698 | 9 |
| Streptococcus faecalis 753 | 0 |
| Corynebacterium pseudodiph. 261 (9742) | 20 |
| Streptococcus faecium 2820 | 26 |
| Streptococcus agalactiae 2875 | 27 |
| Proteus vulgaris 1012 | 15 |
| Pseudomonas aeruginosa 979 | 11 |
| Serratia marcescens 252 (990) | 16 |
| Alcaligenes faecalis 10 (213) | 17 |
| Brucella bronchiseptica 965 (4617) | 16 |
| Salmonella gallinarum 1287 | 15 |
| Vibrio percolans 1272 (8461) | 21 |
| Xanthomonas vesicatoria 815 | 12 |
| Proteus vulgaris 838 (21100) | 23 |
| Escherichia coli 1418 | 15 |
| Pseudomonas stutzeri 1231 (11607) | 13 |
| Klebsiella pneumoniae 1264 | 18 |
| Aerobacter aerogenes 835 | 12 |
| Erwinia atroseptica (4446) | 12 |
| Pseudomonas aeruginosa 2824 | 0 |
| Escherichia coli 60 (9637) | 12 |
| Vibrio percolans 2566 (Res. ceph. C) | 17 |
| Proteus vulgaris 2112 (episome) | 17 |
| Proteus mirabilis 3126 | 14 |
| Vibrio percolans 1272 + $10^5$ u/ml. penicillinase | 21 |

A21A is a valuable antibiotic active against various gram-positive and gram-negative bacteria and, accordingly, finds utility in human and veterinary medicine. The compound of this invention can be used as an antibacterial drug for treating infections caused by gram-positive or gram-negative bacteria, for example against *Staphyloccus aureus, Proteus mirabilis, Escherichia coli, Klebsiella pneumoniae, Pseudomonas aeruginosa* and *Serratia marcescens,* and *mycoplasma gallisepticum.*

A21A is useful both as an antibiotic and as a growth-improvement agent in animals. As a growth-improvement agent, the growth rate and feed efficiency are improved in the animals that are administered the A21A.

A21A can be used as an antibiotic, for example, in the form of pharmaceutical preparations which contain it in admixture or conjunction with an organic or inorganic, solid or liquid pharmaceutical excipient suitable for oral or parenteral administration. Suitable excipients are substances that do not react with the antibiotic, for example, water, gelatin, lactose, starches, stearyl alcohol, magnesium stearate, talcum, vegetable oils, benzyl alcohols, gums, propyleneglycol, polyalkyleneglycols, white petroleum jelly, cholesterol or other known medicinal excipients. The pharmaceutical preparations may be, for example, tablets, or capsules, or in liquid form solutions, suspensions or emulsions. They may be sterilized and/or contain assistants, such as preserving, stabilizing, wetting or emulsifying agents; solution promoters, salts for regulating the osmotic pressure or buffers.

Where it is desired to administer the antibiotic in dry, solid unit dosage form, capsules, boluses or tablets containing the desired amount of antibiotic are employed. These dosage forms are prepared by intimately and uniformly mixing the active ingredient with suitable finely divided diluents, fillers, disintegrating agents and/or binders such as starch, lactose, talc, magnesium stearate, vegetable gums and the like.

Included in this invention are the non-toxic, pharmaceutically acceptable salts and esters of A21A, for example, the alkali and alkaline earth metal salts such as those derived from sodium, potassium, ammonium and calcium or salts with organic bases, for example, triethylamine, N-ethylpiperidine, dibenzylethylenediamine.

In addition to its use as an antibiotic, A21A is useful as a feed additive to improve the growth of animals such as chickens, sheep and cattle. The use of A21A shortens the time required for bringing animals up to marketable weight.

When A21A is used as a growth improver in animals, it can be administered as a component of the feed of the animals or may be dissolved or suspended in the drinking water.

When A21A is used as a component of the animal feed, it is first formulated as a feed supplement. In such feed supplements, A21A is present in relatively large amounts intimately dispersed in an inert carrier or diluent. The feed supplement can be added directly to the feed or made into a premix by an intermediate dilution or blending step. By inert carrier is meant one that will not react with the antibiotic and one that may be administered safely to animals. Preferably, the carrier is one that is, or may be, an ingredient of the animal ration. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The antibiotic is intimately dispersed throughout the carrier by methods such as grinding, stirring, milling or tumbling. Compositions containing from about 5 to 50% by weight of the antibiotic are particularly suitable as feed supplements.

Examples of typical feed supplements containing A21A dispersed in a solid carrier are:

| | | lbs. |
|---|---|---|
| (A) | A21A | 5 |
| | Wheat Standard Middling | 95 |
| (B) | A21A | 50 |
| | Corn distiller's grains | 50 |

These and similar feed supplements are prepared by uniformly mixing the antibiotic with the carrier.

Such supplements are added to the animal feed in an amount to give the finished feed the concentration of A21A desired for growth improvement. In chickens, A21A is fed at a final concentration of between 10 to 100 parts per million in feed in order to achieve the desired growth-improvement result.

In the above discussion, A21A is mixed with an edible carrier in a feed supplement, in a so-called premix or in the final feedstuff. This is the preferred method of administering the A21A. An alternate method is to dissolve or suspend the A21A in the drinking water of the animals. The quantity that may be suspended in the water without undue settling is limited depending upon the solubility of the salt or ester formed of the A21A. Emulsifiers or surface active agents may be employed for this latter purpose to increase the solubility.

It will likewise be understood by those skilled in this art that special feed supplement formulations and finished animal feeds containing A21A may also include vitamins, other antibiotics and growth-improvement agents and other nutritional substances.

It will be appreciated that the dosage to be administered depends to a large extent upon the condition and weight of the host. The preferred route of administrating A21A for growth improvement is by admixing in feed.

The novel antibiotic of the invention A21A shows a broad range of antibacterial activity against human pathogens. A21A was dissolved in DMF and diluted with ph 8 m/15 phosphate buffer and then added to brain heart infusion agar supplemented with 5% horse serum. Plates were spot inoculated with $10^{-3}$ dilutions of 16-hour cultures using a Steers replicator. The minimal inhibitory concentration is shown in the following data.

| Organism | Minimal Inhibitory Conc. in mcg/ml | |
|---|---|---|
| | 24 hr. | 48 hr. |
| Bordetella bronchiseptica | 25 | 100 |
| Pasteurella multocida | 1.6 | 3.1 |
| Past. (Yersinia) pseudotuberculosis | 12.5 | 25 |
| Erysipelothrix rhusiopathiae | 250–400 | >400 |
| Serratia | >400* | >400* |
| Enterococcus | >400* | >400* |
| Streptococcus pyogenes | 0.8 | 3.1 |
| Escherichia coli | 150 | 250 |
| Klebsiella pneumoniae | >400* | >400* |
| Diplococcus pneumoniae | 1.6 | 6.2 |
| Paracolobactrum | >400* | >400* |
| Yersinia enterocolitica WA | 50 | 150 |
| Pseudomonas aeruginosa | 250–350 | 250->400 |
| Providencia | 250–350 | 250–350 |
| Corynebacterium pseudotuberculosis | 6.2 | 50 |
| C. pyogenes | ng | 6.2 |
| Haemophilus influenzae | 1.6 | 1.6 |
| Moraxella bovis | 0.4 | 0.4< |
| Salmonella typhimurium | 200 | >400* |
| Shigella | 100 | 200 |
| Staphylococcus aureus | 400* | >400* |

\* - Marked reduction of growth at lower levels.
ng - No growth on nonmedicated agar after 24 hrs., growth after 48 hrs. incubation.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of an identical product should be construed as constituting an analogous method. The described processes are capable of wide variation and modification and any minor departure or extension is considered as being within the skill of the artisan and as falling within the scope of this invention.

EXAMPLE 1

A lyophilized tube containing a culture of Streptomyces filipinensis MA-4581 is opened and aseptically transferred into a few ml. of Davis Salts having the following composition.

| Davis Salts | |
|---|---|
| Sodium citrate | 0.5 g. |
| $K_2HPO_4$ | 7.0 g. |
| $KH_2PO_4$ | 3.0 g. |
| $(NH_4)_2SO_4$ | 1.0 g. |
| $MgSO_4 \cdot 7H_2O$ | 0.1 g. |
| Distilled Water | 1000 ml. |

A portion of the above medium is used to inoculate a baffled, 250-ml. Erlenmeyer flask containing 54 ml. of Medium A having the following composition.

| Medium A | |
|---|---|
| Ardamine pH | 10.0 g. |
| Cerelose | 10.0 g. |
| $KH_2PO_4$ | .182 g. |
| $Na_2HPO_4$ | .190 g. |
| $MgSO_4 \cdot 7H_2O$ | 0.05 g. |
| Distilled Water | 1000 ml. |
| pH 6.5 | |

This flask is inoculated at 28° C., 220 RPM until growth is satisfactory (1–4 days). A portion of this flask (2 ml.) is used to inoculate unbaffled, 250-ml. Erlenmeyer flask containing 44 ml. of Medium B having the following composition.

| Medium B | |
|---|---|
| Tomato Paste | 4.0 g. |
| Oat Flour | 15.0 g. |
| Distilled Water | 1000 ml. |
| pH 6.0 | |

After three days incubation at 28° C., 220 RPM, a portion of one flask is submitted for bio-activity assay.

The broth is active against both gram-positive and gram-negative organisms. The broth gives a 19 mm. zone of inhibition against Alcaligenes faecalis ATCC 213, 23 mm. zone against Proteus vulgaris ATCC 21100, and 18 mm. zone against Corynebacterium pseudodiph. ATCC 9742 using ¼ inch assay discs on standard assay plates.

EXAMPLE 2

A lyophilized culture of Streptomyces filipinensis MA-4581 is inoculated into 40 ml. seed medium in a 250-ml. three-baffled Erlenmeyer flask and incubated at 28° C. for three days on a rotary shaker operating at 220 rpm. The seed medium has the following composition:

| Seed Medium | |
|---|---|
| Corn Meal | 20 g. |
| Distiller's Solubles | 10 g. |
| 4s Soybean Meal | 15 g. |
| Sodium Citrate | 4 g. |
| $CaCl_2 \cdot 2H_2O$ | 0.5 g. |
| $MgSO_4 \cdot 7H_2O$ | 0.1 g. |
| $CoCl_2 \cdot 6H_2O$ | 0.01 g. |
| $FeSO_4 \cdot H_2O$ | 0.01 g. |
| Polyglycol 2000 | 0.25% by volume |
| Distilled $H_2O$ | 1000 ml. |
| pH adjusted to 6.5 | |

One ml. of the seed medium culture is inoculated into each of 12 flasks of production medium. The production flasks consist of 40 ml. of production medium contained in 250-ml. unbaffled Erlenmeyer flasks to which one drop of Polyglycol 2000 is added before autoclaving at 15 pounds per square inch (psi) for 20 minutes. The composition of the production medium is the following:

| Production Medium | |
|---|---|
| Tomato paste | 40.0 g. |
| Oatmeal (ground) | 15.0 g. |
| Distilled H₂O | 1000 ml. |
| pH adjusted to 6.0 with sodium hydroxide. | |

The flasks are incubated at 28° C. for five days on a rotary shaker operating at 220 rpm.

At the end of this period, the contents of 11 of the flasks are pooled and brought to pH 5.0 with hydrochloric acid. Four hundred and seventy ml. of chloroform is added and the mixture is extracted for 20 minutes.

The chloroform phase is separated by centrifugation from the spent broth and dried over 8 g. of anhydrous magnesium sulfate. The dried chloroform extract is then evaporated to near dryness and washed with 20 ml. of hexane to remove lipids and precipitate the A21A. The precipitate is dried and yield 4 mg. of the antibiotic A21A.

EXAMPLE 3

A 1-ml. frozen aliquot of seed culture containing MA-4581 is grown at 28° C. for two days on a rotary shaker operating at 220 rpm in a 250-ml. baffled Erlenmeyer flask containing 40 ml. of Primary Yeast Medium having the following composition:

| Primary Yeast Medium | |
|---|---|
| Primary yeast | 10 g. |
| Distilled H₂O | 1000 ml. |
| pH adjusted to 7.3 with sodium hydroxide. | |

1 Ml. of seed medium culture is used to inoculate 25 flasks of Production Medium having the following composition:

| Production Medium | |
|---|---|
| Tomato paste | 40.0 g. |
| Oatmeal (ground) | 15.0 g. |
| Distilled H₂O | 1000 g. |
| pH adjusted to 6.0 with sodium hydroxide. | |

The production flasks are grown at 28° C. for five days on a rotary shaker operating at 220 rpm.

At the end of five days, the contents of the flasks are pooled and brought to pH 5 with hydrochloric acid. The broth is extracted with chloroform for about 20 minutes. The chloroform phase is separated by centrifugation from the spent broth and dried over anhydrous magnesium sulfate. The dried chloroform extract is then evaporated to near dryness and washed with hexane to remove lipids and also precipitate the A21A. The precipitate is dried to yield 9.8 of the antibiotic A21A.

EXAMPLE 4

A slant culture of *Streptomyces filipinensis* MA-4581 is grown on Seed Medium solidified with 2% agar having the following composition;

| Seed Medium | |
|---|---|
| Corn Meal | 20 g. |

| Seed Medium | |
|---|---|
| Distiller's Solubles | 10 g. |
| 4s Soybean Meal | 15 g. |
| Sodium Citrate | 4 g. |
| CaCl₂ . 2H₂O | 0.5 g. |
| MgSO₄ . 7H₂O | 0.1 g. |
| CoCl₂ . 6H₂O | 0.01 g. |
| FeSO₄ . H₂O | 0.01 g. |
| Polyglycol 2000 | 0.25% by volume |
| Distilled H₂O | 1000 ml. |
| pH adjusted to 6.5 | |

The culture is inoculated into a 250-ml., three-baffled Erlenmeyer flask containing 50 ml. of Primary Yeast Medium made with tap water and incubated for two days at 27° C.

| Primary Yeast Medium | |
|---|---|
| Primary yeast | 10 g. |
| Tap water | 1000 ml. |
| pH adjusted to 7.3 with sodium hydroxide. | |

The entire culture is used to inoculate a 2-liter baffled Erlenmeyer flask containing 500 ml. of Primary Yeast Medium for one day. This second stage seed culture is then used to inoculate a vessel containing 350 liters of Production Medium having the following composition:

| Production Medium | |
|---|---|
| Tomato paste | 40.0 g. |
| Oatmeal (ground) | 15.0 g. |
| Distilled water | 1000 ml. |
| pH adjusted to 6.0 with sodium hydroxide. | |

The Production Medium is incubated at 27° C. under aeration conditions. After five days, two 5-gallon samples of the fermentation broth is adjusted to pH 5.0 using hydrochloric acid. The broth is then filtered through a 200-g. bed of Celite, and the filtrate is extracted with two 1¼-gallon batches of ethyl acetate. The ethyl acetate extracts are pooled, dried, concentrated then shaken with hexane, thus precipitating the A21A product. The precipitate is dried to give 3.12 g. of A21A product.

What is claimed is:

1. A method of producing antibiotic A21A which comprises cultivating a A21A-producing strain of *Streptomyces filipinensis* in a fermentation broth containing assimilable sources of carbohydrates, nitrogen and inorganic salts under aerobic conditions until a substantial amount of A21A is produced in the fermentation broth and recovering said antibiotic.

2. The method of claim 1 wherein the *Streptomyces filipinensis* has NRRL 11,044.

3. The method of claim 1 wherein the whole fermentation broth is extracted with a water immiscible polar or hydroxylic solvent.

4. The method of claim 3 wherein the solvent is selected from the group consisting of methyl formate, ethyl formate, methyl acetate, ethyl acetate, n-butyl acetate, isobutyl acetate, ethyl proprionate, methyl ethyl ketone, cyclohexanone, chloroform, methylene chloride, carbon tetrachloride, ethylene dichloride, 1-chloro-2,2-dimethylpropane, tetrachloroethylene, bromoform and n-butanol.

5. The method of claim 4 wherein the polar or hydroxylic solvent is chloroform, methyl ethyl ketone or ethyl acetate.

6. The method of claim 5 wherein the antibiotic A21A is recovered in substantially pure form.

* * * * *